US008696552B2

(12) United States Patent
Whitman (10) Patent No.: US 8,696,552 B2
(45) Date of Patent: Apr. 15, 2014

(54) SELF-CONTAINED STERILIZABLE SURGICAL SYSTEM

(75) Inventor: Michael P. Whitman, New Hope, PA (US)

(73) Assignee: Covidien LP, Mansfield, MA (US)

( * ) Notice: Subject to any disclaimer, the term of this patent is extended or adjusted under 35 U.S.C. 154(b) by 988 days.

(21) Appl. No.: 10/676,046

(22) Filed: Sep. 30, 2003

(65) Prior Publication Data

US 2004/0111012 A1 Jun. 10, 2004

Related U.S. Application Data

(60) Provisional application No. 60/415,313, filed on Sep. 30, 2002.

(51) Int. Cl.
*A61B 1/005* (2006.01)
*A61B 1/05* (2006.01)
*A61B 1/06* (2006.01)
*A61B 1/00* (2006.01)

(52) U.S. Cl.
CPC ........... *A61B 1/0052* (2013.01); *A61B 1/00128* (2013.01); *A61B 1/00142* (2013.01); *A61B 1/05* (2013.01); *A61B 1/0684* (2013.01); *A61B 1/0676* (2013.01)
USPC ........... 600/146; 600/133; 600/136; 600/152; 600/179

(58) Field of Classification Search
USPC ......... 600/133, 136, 179, 146, 152, 178, 130, 600/131, 129, 156
See application file for complete search history.

(56) References Cited

U.S. PATENT DOCUMENTS

| 3,256,875 A | 6/1966 | Tsepelev et al. |
| 3,858,577 A | 1/1975 | Bass et al. |
| 3,859,986 A | 1/1975 | Okada et al. |
| 4,027,510 A | 6/1977 | Hiltebrandt |

(Continued)

FOREIGN PATENT DOCUMENTS

| DE | 42 13 426 | 10/1992 |
| DE | 196 26 433 | 1/1998 |

(Continued)

OTHER PUBLICATIONS

New York Magazine, Jun. 10, 2002 The Best Doctors in New York, p. 80.

(Continued)

*Primary Examiner* — John P Leubecker (57) ABSTRACT

A self-contained surgical, e.g., endoscope, system. The surgical, e.g., endoscope, system may include a sterilizable shaft having a light source and/or an image capture device mounted at the distal end of the shaft or connected to the distal end of the shaft by fiber optics. The light source is a light emitting diode or an array of light emitting diodes, and may have its own power source located at the distal end of the shaft. The shaft includes a working channel, an irrigation/aspiration channel, and an electric cable. The shaft is coupled at its proximal end to a control module having a video processor and an integrally-mounted display screen for displaying image data from the image capture device. The control module may also include an irrigation/aspiration system, a control unit, and a controller. The control module is coupled to a power module. The power module includes steering motors connected to steering cables in the shaft. In addition, the power module includes drive motors and a power source.

23 Claims, 10 Drawing Sheets

(56) References Cited

U.S. PATENT DOCUMENTS

| | | |
|---|---|---|
| 4,085,756 A | 4/1978 | Weaver |
| 4,198,960 A | 4/1980 | Utsugi |
| 4,250,873 A | 2/1981 | Bonnet |
| 4,273,109 A | 6/1981 | Enderby |
| 4,273,111 A | 6/1981 | Tsukaya |
| 4,286,585 A | 9/1981 | Ogawa |
| 4,367,729 A | 1/1983 | Ogiu |
| 4,379,457 A | 4/1983 | Gravener et al. |
| 4,402,311 A | 9/1983 | Hattori |
| 4,445,892 A | 5/1984 | Hussein et al. |
| 4,448,188 A | 5/1984 | Loeb |
| 4,494,549 A | 1/1985 | Namba et al. |
| 4,499,895 A | 2/1985 | Takayama |
| 4,559,928 A | 12/1985 | Takayama |
| 4,593,679 A | 6/1986 | Collins |
| 4,672,961 A | 6/1987 | Davies |
| 4,674,515 A | 6/1987 | Andou et al. |
| 4,732,156 A | 3/1988 | Nakamura |
| 4,742,815 A | 5/1988 | Ninan et al. |
| 4,756,309 A | 7/1988 | Sachse et al. |
| 4,760,840 A | 8/1988 | Fournier, Jr. et al. |
| 4,815,469 A | 3/1989 | Cohen et al. |
| 4,819,632 A | 4/1989 | Davies |
| 4,880,015 A | 11/1989 | Nierman |
| 4,884,133 A * | 11/1989 | Kanno et al. ............... 348/68 |
| 4,890,602 A | 1/1990 | Hake |
| 4,893,613 A | 1/1990 | Hake |
| 4,895,138 A * | 1/1990 | Yabe ............................ 600/110 |
| 4,907,588 A | 3/1990 | Burston |
| 4,907,973 A | 3/1990 | Hon |
| 4,928,699 A | 5/1990 | Sasai |
| 4,930,494 A | 6/1990 | Takehana et al. |
| 4,941,454 A | 7/1990 | Wood et al. |
| 4,941,456 A * | 7/1990 | Wood et al. ................. 600/152 |
| 4,944,443 A | 7/1990 | Oddsen et al. |
| 4,955,882 A | 9/1990 | Hakky |
| 4,976,710 A | 12/1990 | Mackin |
| 4,982,726 A | 1/1991 | Taira |
| 4,994,060 A | 2/1991 | Rink et al. |
| 5,133,713 A | 7/1992 | Huang et al. |
| 5,134,281 A | 7/1992 | Bryenton et al. |
| 5,186,714 A | 2/1993 | Boudreault et al. |
| 5,197,649 A | 3/1993 | Bessler et al. |
| 5,201,325 A | 4/1993 | McEwen et al. |
| 5,201,730 A | 4/1993 | Easley et al. |
| 5,217,003 A | 6/1993 | Wilk |
| 5,243,967 A | 9/1993 | Hibino |
| 5,251,613 A | 10/1993 | Adair |
| 5,258,008 A | 11/1993 | Wilk |
| 5,305,121 A | 4/1994 | Moll |
| 5,306,234 A | 4/1994 | Johnson |
| 5,322,055 A | 6/1994 | Davison et al. |
| 5,330,486 A | 7/1994 | Wilk |
| 5,333,772 A | 8/1994 | Rothfuss et al. |
| 5,354,266 A | 10/1994 | Snoke |
| 5,368,015 A | 11/1994 | Wilk |
| 5,383,880 A | 1/1995 | Hooven |
| 5,395,030 A | 3/1995 | Kuramoto et al. |
| 5,396,879 A * | 3/1995 | Wilk et al. ................... 600/152 |
| 5,411,508 A | 5/1995 | Bessler et al. |
| 5,437,636 A | 8/1995 | Snoke et al. |
| 5,441,507 A | 8/1995 | Wilk |
| 5,460,182 A | 10/1995 | Goodman et al. |
| 5,496,269 A | 3/1996 | Snoke |
| 5,531,687 A | 7/1996 | Snoke et al. |
| 5,540,711 A | 7/1996 | Kieturakis et al. |
| 5,603,688 A | 2/1997 | Upsher |
| 5,604,531 A | 2/1997 | Iddan et al. |
| 5,609,560 A | 3/1997 | Ichikawa et al. |
| 5,630,782 A | 5/1997 | Adair |
| 5,630,783 A * | 5/1997 | Steinberg ..................... 600/158 |
| 5,653,677 A | 8/1997 | Okada et al. |
| 5,662,680 A | 9/1997 | Desai |
| 5,667,473 A | 9/1997 | Finn et al. |
| 5,667,478 A | 9/1997 | McFarcin et al. |
| 5,667,517 A | 9/1997 | Hooven |
| 5,797,835 A | 8/1998 | Green |
| 5,797,944 A | 8/1998 | Nobles et al. |
| 5,815,640 A | 9/1998 | Wang et al. |
| 5,855,583 A | 1/1999 | Wang et al. |
| 5,857,996 A | 1/1999 | Snoke |
| 5,865,728 A | 2/1999 | Moll et al. |
| 5,868,760 A | 2/1999 | McGuckin, Jr. |
| 5,878,193 A | 3/1999 | Wang et al. |
| 5,882,331 A | 3/1999 | Sasaki |
| 5,907,664 A | 5/1999 | Wang et al. |
| 5,920,390 A | 7/1999 | Farahi et al. |
| 5,935,143 A | 8/1999 | Hood |
| 5,941,818 A | 8/1999 | Hori et al. |
| 5,954,634 A | 9/1999 | Igarashi |
| 5,954,642 A | 9/1999 | Johnson et al. |
| 5,968,060 A | 10/1999 | Kellogg |
| 5,989,184 A | 11/1999 | Blair |
| 5,989,274 A | 11/1999 | Davison et al. |
| 5,993,378 A | 11/1999 | Lemelson |
| 5,995,645 A | 11/1999 | Soenksen et al. |
| RE36,434 E * | 12/1999 | Hamlin et al. ................. 600/109 |
| 6,015,969 A | 1/2000 | Nathel et al. |
| 6,019,719 A | 2/2000 | Schulz et al. |
| 6,027,515 A | 2/2000 | Cimino |
| 6,056,735 A | 5/2000 | Okada et al. |
| 6,063,095 A | 5/2000 | Wang et al. |
| 6,066,090 A | 5/2000 | Yoon |
| 6,068,627 A | 5/2000 | Orzulak et al. |
| 6,068,647 A | 5/2000 | Witt et al. |
| 6,069,689 A | 5/2000 | Zeng et al. |
| 6,074,402 A | 6/2000 | Peifer et al. |
| 6,077,285 A | 6/2000 | Boukhny |
| 6,083,191 A | 7/2000 | Rose |
| 6,099,466 A | 8/2000 | Sano et al. |
| 6,099,537 A | 8/2000 | Sugai et al. |
| 6,117,152 A | 9/2000 | Huitema |
| 6,124,597 A | 9/2000 | Shehada et al. |
| 6,126,591 A | 10/2000 | McGarry et al. |
| 6,134,003 A | 10/2000 | Tearney et al. |
| 6,139,561 A | 10/2000 | Shibata et al. |
| 6,142,930 A | 11/2000 | Ito et al. |
| 6,159,225 A | 12/2000 | Makower |
| 6,163,378 A | 12/2000 | Khoury |
| 6,208,749 B1 | 3/2001 | Gutkowicz-Krusin et al. |
| 6,208,887 B1 | 3/2001 | Clarke |
| 6,211,904 B1 | 4/2001 | Adair et al. |
| 6,215,550 B1 | 4/2001 | Baer et al. |
| 6,224,227 B1 | 5/2001 | Klootz |
| 6,236,502 B1 | 5/2001 | Kitajima |
| 6,238,386 B1 | 5/2001 | Miller et al. |
| 6,240,305 B1 | 5/2001 | Tsuchiya |
| 6,244,809 B1 | 6/2001 | Wang et al. |
| 6,245,058 B1 | 6/2001 | Suzuki |
| 6,251,101 B1 | 6/2001 | Glockler |
| 6,260,994 B1 * | 7/2001 | Matsumoto et al. ........... 362/574 |
| 6,263,227 B1 | 7/2001 | Boggett et al. |
| 6,319,199 B1 | 11/2001 | Sheehan et al. |
| 6,331,181 B1 | 12/2001 | Tierney et al. |
| 6,364,888 B1 | 4/2002 | Niemeyer et al. |
| 6,371,907 B1 * | 4/2002 | Hasegawa et al. ............. 600/146 |
| 6,398,726 B1 | 6/2002 | Ramans et al. |
| 6,442,432 B2 | 8/2002 | Lee |
| 6,443,973 B1 | 9/2002 | Whitman |
| 6,447,444 B1 | 9/2002 | Avni et al. |
| 6,459,822 B1 | 10/2002 | Hathaway et al. |
| 6,471,637 B1 | 10/2002 | Chatenever et al. |
| 6,488,197 B1 | 12/2002 | Whitman |
| 6,491,201 B1 | 12/2002 | Whitman |
| 6,505,768 B2 | 1/2003 | Whitman |
| 6,517,565 B1 | 2/2003 | Whitman et al. |
| 6,533,157 B1 | 3/2003 | Whitman |
| 6,540,670 B1 * | 4/2003 | Hirata et al. ................... 600/152 |
| 6,599,238 B2 * | 7/2003 | Ooshima et al. ............... 600/121 |
| 6,612,981 B2 * | 9/2003 | Onishi et al. ................... 600/118 |
| 6,612,982 B1 * | 9/2003 | Ouchi .............................. 600/139 |
| 6,648,816 B2 | 11/2003 | Irion et al. ....................... 600/173 |
| 6,692,430 B2 * | 2/2004 | Adler ............................... 600/109 |
| 6,770,027 B2 * | 8/2004 | Banik et al. ..................... 600/146 |

(56) References Cited

U.S. PATENT DOCUMENTS

| | | | |
|---|---|---|---|
| 6,793,652 B1 * | 9/2004 | Whitman et al. | 606/1 |
| 6,796,939 B1 * | 9/2004 | Hirata et al. | 600/179 |
| 6,802,809 B2 * | 10/2004 | Okada | 600/146 |
| 2001/0000672 A1 | 5/2001 | Yamakita et al. | |
| 2001/0001812 A1 | 5/2001 | Valley et al. | |
| 2001/0016725 A1 | 8/2001 | Valley et al. | |
| 2001/0031975 A1 | 10/2001 | Whitman et al. | |
| 2001/0051762 A1 * | 12/2001 | Murata et al. | 600/118 |
| 2002/0026094 A1 | 2/2002 | Roth | |
| 2002/0032451 A1 | 3/2002 | Tierney et al. | |
| 2002/0032452 A1 | 3/2002 | Tierney et al. | |
| 2002/0042620 A1 | 4/2002 | Julian et al. | |
| 2002/0049454 A1 | 4/2002 | Whitman et al. | |
| 2002/0055795 A1 | 5/2002 | Niemeyer et al. | |
| 2002/0092533 A1 | 7/2002 | Boyd et al. | |
| 2002/0159529 A1 | 10/2002 | Wang et al. | |
| 2002/0165444 A1 | 11/2002 | Whitman | |
| 2003/0018237 A1 * | 1/2003 | Okada | 600/146 |
| 2003/0018238 A1 * | 1/2003 | Obata et al. | 600/179 |
| 2003/0092965 A1 * | 5/2003 | Konomura et al. | 600/146 |
| 2003/0195389 A1 * | 10/2003 | Motoki et al. | 600/146 |
| 2004/0054259 A1 * | 3/2004 | Hasegawa et al. | 600/152 |
| 2004/0267095 A1 * | 12/2004 | Miyake et al. | 600/175 |

FOREIGN PATENT DOCUMENTS

| | | |
|---|---|---|
| DE | 1962643 A1 | 1/1998 |
| EP | 0 341 719 | 11/1989 |
| EP | 0 667 115 | 8/1995 |
| EP | 0 774 231 | 5/1997 |
| EP | 0978251 A1 | 2/2000 |
| GB | 2128881 | 5/1984 |
| GB | 2 291 980 | 2/1996 |
| GB | 2291980 | 2/1996 |
| JP | 59 223 079 | 12/1984 |
| WO | WO 82/03545 | 10/1982 |
| WO | WO 83/00992 | 3/1983 |
| WO | WO 92/16141 | 10/1992 |
| WO | WO 93/15648 * | 8/1993 |
| WO | WO 98/32380 | 7/1998 |
| WO | WO 02/55126 | 6/1999 |
| WO | WO 99/30610 | 6/1999 |
| WO | WO 99/32028 | 7/1999 |
| WO | WO 00/22975 | 4/2000 |
| WO | WO 00/76391 | 12/2000 |
| WO | WO 01/10291 | 2/2001 |
| WO | WO 01/35813 | 5/2001 |
| WO | WO 01/62163 | 8/2001 |
| WO | WO 02/055126 | 7/2002 |
| WO | WO 03/077769 | 9/2003 |

OTHER PUBLICATIONS

"Manometric Findings in Dysphagia Secondary to Left Atrial Dilatation Digestive Diseases and Sciences", vol. 36, May 1991, M. Cappell.

"Case Report: Late Pulmonary Embolization . . . ", Apr. 1985, E.D. Mayer et al.

"Fiberoptic examination of the inferior vena cava . . . ", Thorac. Cardiovascular Surgeon, 33, Jun. 1990, A. R. Hartman.

"Media Stinoscope: Another Use." Journal of Cardio Surgery, 27, Mar. 1986, P. R. Behl.

"Special Pacemaker Catheter Techniques: The Transmediastinal Placement of Sensing Electrodes", Apr. 1976, Kleinert et al.

"Endobronchial Resection with the ND-Yag Laser—Two Year Experience in an Australian Unit", Australia/New Zealnd Journal of Medicine, Apr. 1990, R. J. Pierce.

"Cardiovascular Fiberoptic Endoscopy: Development and Clinical Application", Apr. 1980, T. Tanabe et al.

European Search Report for EP 11 00 1302 dated May 4, 2011.

* cited by examiner

SELF-CONTAINED STERILIZABLE SURGICAL SYSTEM

CROSS-REFERENCE TO RELATED APPLICATIONS

This application claims the benefit under 35 U.S.C. §119 (e) of U.S. Provisional Patent Application No. 60/415,313, filed on Sep. 30, 2002, which is expressly incorporated herein by reference in its entirety.

FIELD OF THE INVENTION

The present invention relates to a surgical system. More specifically, the present invention relates to a self-contained, sterilizable surgical system, such as an endoscope system.

BACKGROUND

There are various different surgical systems that enable a surgical procedure or a surgical site to be viewed. One such type of surgical device is an endoscope. Such a device may be inserted into a patient's body during a surgical procedure to illuminate, view and/or manipulate a surgical site within the patient's body. Conventional endoscopes typically employ a flexible endoscope shaft, a first end of which is insertable into a patient's body. The shaft has a camera mounted at the first end and is connected at its second end to a power source for providing power to the camera. In addition, the shaft has a fiberoptic bundle that runs therethrough and connects to a light source outside of the patient's body. The light source is powered by another power source and the light from the light source is conveyed from the second end, through the fiberoptic bundle in the shaft, to the first end in order to illuminate a surgical site within the patient's body. In addition, the second end of the endoscope is connected to a television monitor, having still another power source, in order to display the images received by the camera.

Thus, conventional surgical systems of this type, e.g., endoscope systems, are typically bulky, complex and difficult to maneuver.

SUMMARY

The present invention relates to a surgical system, e.g., an endoscope system. According to one embodiment, an endoscope system includes a shaft having a light source and/or an image capture device, e.g., a camera, each of which may be mounted at the distal end of the shaft or which may be connected to the distal end of the shaft by fiber optics. The light source may be a light emitting diode or an array of light emitting diodes, and may have its own power source located at the distal end of the shaft. The shaft has a sheath that is sealed so as to be sterilizable, e.g., autoclavable. Advantageously, the light source and/or the image capture device are also sealed within the distal end of the shaft so as to be sterilizable, e.g., autoclavable. The shaft also includes a working channel for permitting the passage of tools through the shaft, an irrigation/aspiration channel for permitting fluid to be transmitted through the shaft, and an electric cable for transmitting data or power through the shaft.

The shaft is coupled, either fixedly or detachably, at its proximal end to a control module having a video processor. Preferably, the control module is sterilizable, e.g., autoclavable. Image data received by the image capture device is transmitted via a data transfer cable of the electric cable in the shaft to the video processor and is displayed on an display screen integrally mounted to the control module. The control module may include an irrigation/aspiration system for conveying fluid through the irrigation/aspiration channel of the shaft. The control module may also include a control unit, which enables a user to control certain functions of the endoscope system, as well as a controller, which automatically controls certain functions of the endoscope system.

The control module is coupled to a power module. The power module includes steering motors connected to steering cables in the shaft. In addition, the power module includes drive motors for driving, e.g., the irrigation/aspiration system, the steering motors, etc. The power module may also include a power source for providing power to the motors, the controller, the light source, the image capture device, etc. In one embodiment, the control module and the power module are contained in a single unit.

DETAILED DESCRIPTION

Figure 1:
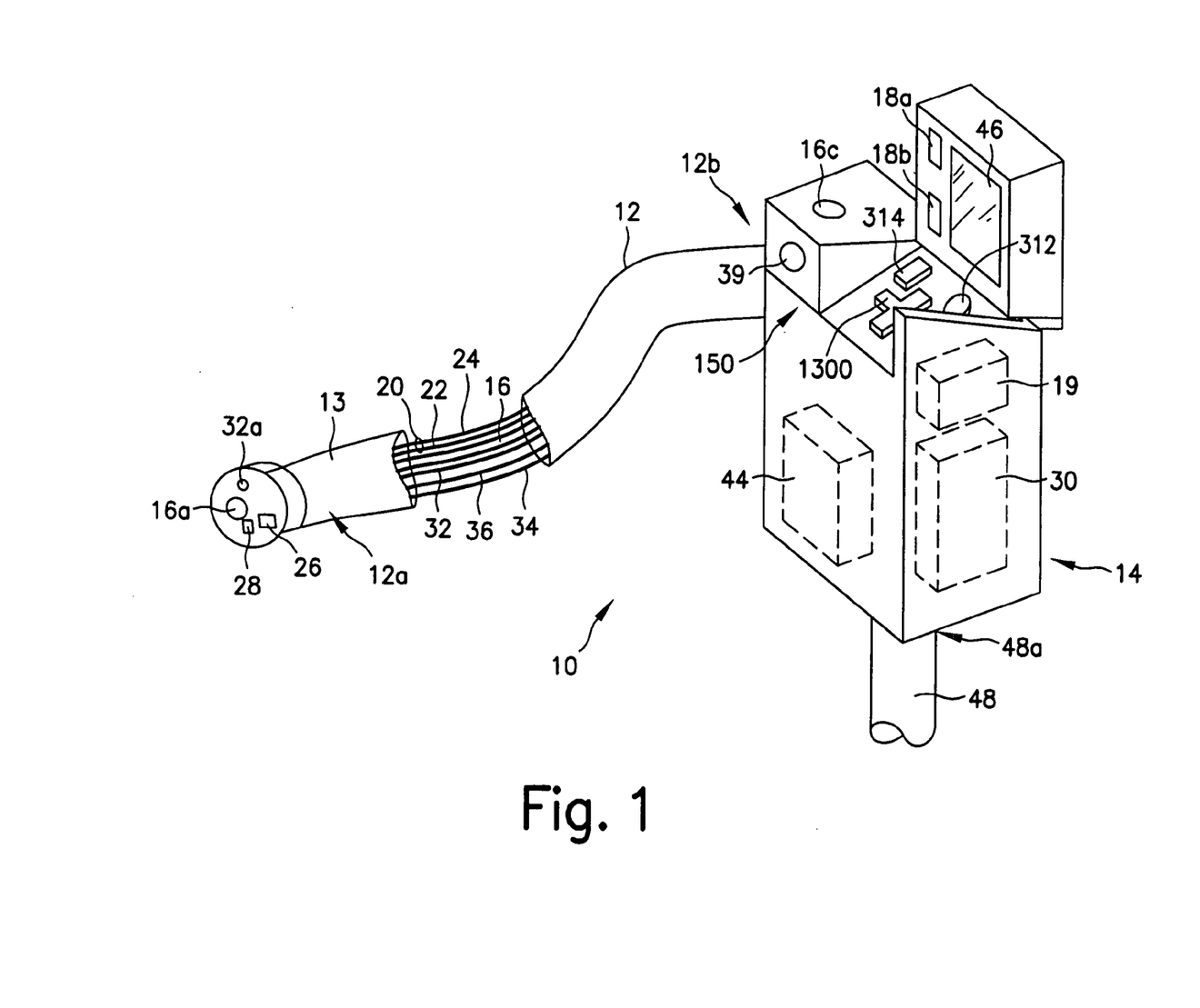
FIG. 1 is a perspective view of several components of an endoscope system, according to one example embodiment of the present invention.

One example embodiment of a surgical system, in this case an endoscope system 10, according to the present invention is illustrated in FIGS. 1 to 7. FIG. 1 illustrates several components of the endoscope system 10, including a shaft 12 and a control module 14 to which the shaft 12 is attached. Although the example embodiment described herein describes the shaft 12 as being fixedly attached to the control module 14, it is recognized that, in alternative embodiments of the present invention, the shaft 12 may be detachably coupled to the control module 14. Furthermore, it should be recognized that while the surgical system 10 is described in connection with an endoscope, the surgical system may also be employed in connection with a proctoscope, an anoscope, etc.

According to one embodiment, the shaft 12 includes a tubular sheath 13, which may include a coating or other sealing arrangement to provide a fluid-tight seal between an interior region of the shaft 12 and the environment. The sheath 13 may be formed of a tissue-compatible, sterilizable elastomeric material. Preferably, the sheath 13 may be formed of a material that is autoclavable. In addition, the sheath 13 may be formed of a material having a high or relatively high lubricity.

For instance, the sheath 13 may be formed of a material such as Teflon™ (i.e., a fluoropolymer, e.g., polytetrafluoroethylene—"PTFE"), silicone, a Teflon™/silicone combination, such as, for example, SIL-KORE™ (made by W. L. Gore & Associates), "EPTFE", e.g., expanded teflon, etc. Other suitable materials and sealing arrangements that may be employed are described in further detail in Applicants' co-pending U.S. patent application Ser. No. 10/099,634, filed on Mar. 15, 2002, which is expressly incorporated herein by reference in its entirety.

In this embodiment, the shaft 12 has a distal end 12a, which is insertable into a patient's body, and a proximal end 12b, which is coupled, e.g., either fixedly or detachably, to the control module 14. In this embodiment, both a light source 26 and an image capture device 28 are mounted on the distal end 12a of the shaft 12. In other example embodiments, the light source 26 and/or the image capture device 28 are mounted in the control module 14. If the light source 26 is mounted in the control module 14, the light may be transmitted from the light source 26 to the distal end 12a of the shaft 12 via fiber optics. If the image capture device 28 is mounted in the control module 14, the image data (including light reflected within a body, for example) may be transmitted to the image capture device 28 from the distal end 12a of the shaft 12 via fiber optics.

The image capture device 28 may include a lens and an image sensor, e.g., a light sensitive device such as a CCD or CMOS-type image sensor, that is positioned to capture an image via the lens. In one embodiment, the image capture arrangement 28 may further include a cleaning arrangement for cleaning debris from the lens. Advantageously, the light source 26 and the image capture device 28 are sealed within the distal end 12a of the shaft 12 such that the light source 26 and the image capture device 28 are also sterilizable, e.g., autoclavable.

According to the embodiment shown in FIG. 1, the shaft 12 also defines an electric cable 20 that extends from the distal end 12a of the shaft 12 to the proximal end 12b of the shaft 12. According to one embodiment of the present invention, the electric cable 20 includes a power transfer cable 22 and a data transfer cable 24. A distal end of the power transfer cable 22 is coupled to the light source 26 and/or to the image capture device 28 that are mounted on the distal end 12a of the shaft. A proximal end of the power transfer cable 22 is coupled to a power source, such as power source 44 disposed in the control module 14 or, alternatively, to a power source 62 disposed in the power module 50 (described in greater detail below in connection with FIG. 2). The power transfer cable 22 may be configured to provide power from the power source 44 or the power source 62 to the light source 26 and/or the image capture device 28.

Figure 8:
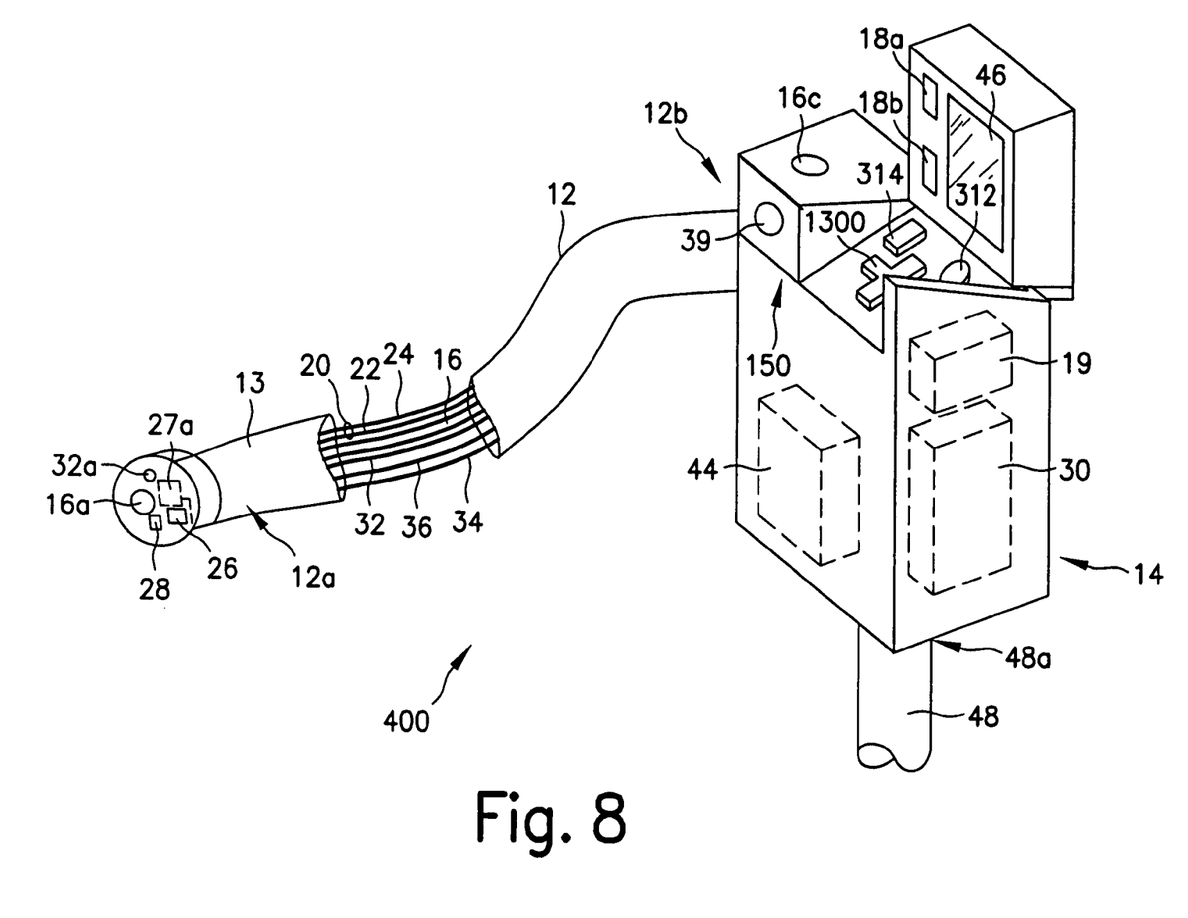
FIG. 8 is a perspective view of several components of an endoscope system, according to another example embodiment of the present invention.

Alternatively or additionally, an additional power source may be mounted at the distal end 12a of the shaft 12 adjacent to the light source 26 and the image capture device 28, and may provide power to the light source 26 and/or the image capture device 28. For instance, FIG. 8 illustrates one embodiment of the present invention, in which an endoscope system 400 has an additional power source 27a that is mounted at the distal end 12a of the shaft 12 adjacent to the light source 26 and the image capture device 28. The additional power source 27a provides power to the light source 26 and/or the image capture device 28. Thus, according to this embodiment, the need for the power transfer cable 22 in the shaft 12 may be eliminated, thereby decreasing the cross-sectional area of the shaft 12 if desired. Since the shaft 12 may during operation be inserted through an incision made by a surgeon in a patient, and since it is generally desirable to minimize the size of such incisions, e.g., for healing purposes, a decrease in the cross-sectional area of the shaft 12 may be advantageous in that it requires a smaller incision for insertion into a patient.

Figure 9:
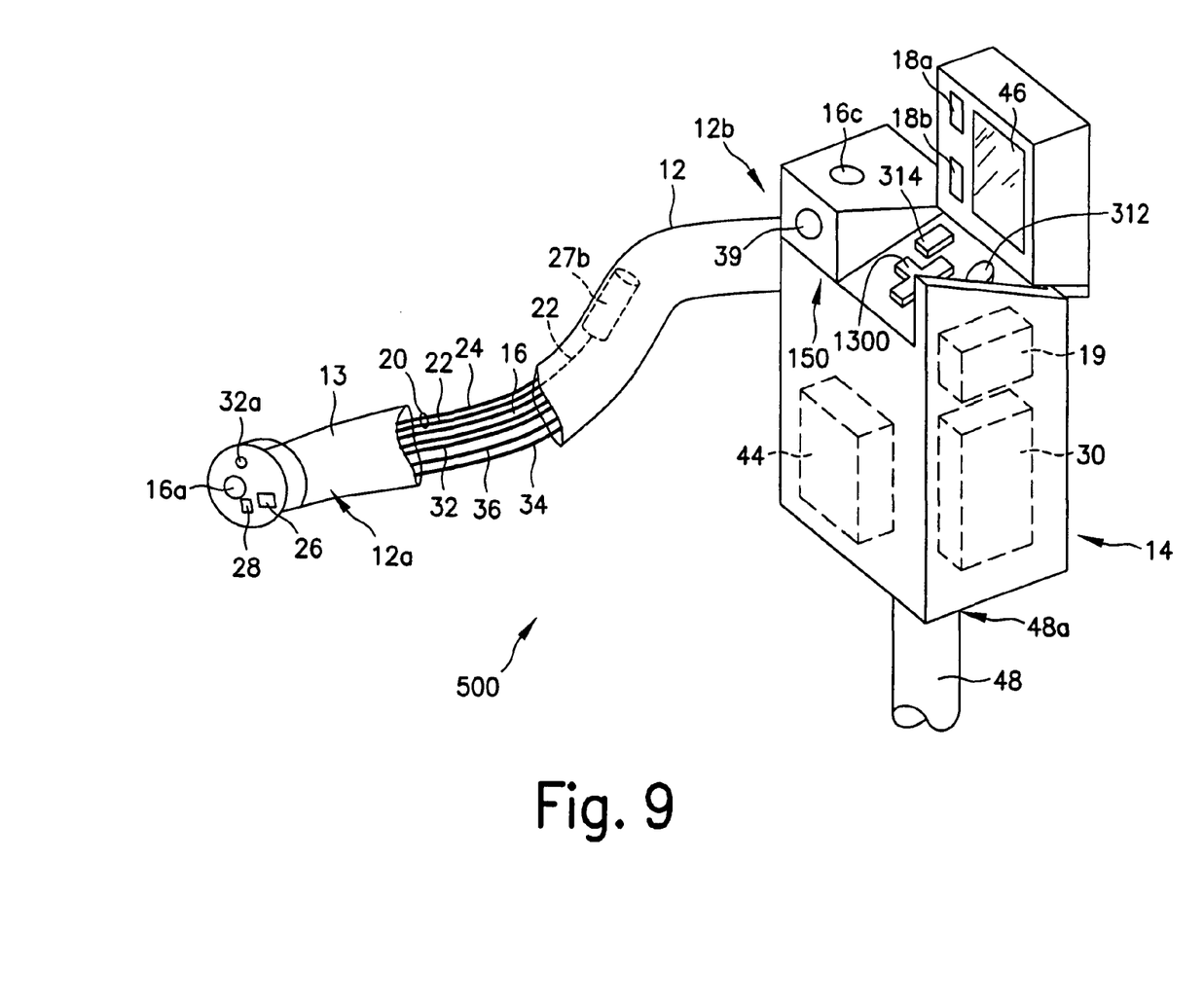
FIG. 9 is a perspective view of several components of an endoscope system, according to still another example embodiment of the present invention.

It should be understood that, according to various other embodiments of the present invention, the power source for the light source 26 and the image capture device 28 may be located at any position along the shaft 12, or may be located at any other position. In those embodiments in which the power source for the light source 26 and the image capture device 28 are located at a position along the shaft 12, the power transfer cable 22 may extend within the shaft 12 between the light source 26 and/or the image capture device 28 and the power source. For instance, FIG. 9 illustrates another embodiment of the present invention, in which an endoscope system 500 has an additional power source 27b that is located within a portion of the shaft 12, between the distal end 12a and the proximal end 12b of the shaft 12. The additional power source 27b provides power to either or both of the light source 26 and the image capture device 28. Thus, according to this embodiment, the need for the power transfer cable 22 in the shaft 12 may be partially eliminated, e.g., in the portion of the shaft between the additional power source 27b and the proximal end 12b of the shaft 12.

Referring back to FIG. 1, the light source 26 mounted to the distal end 12a of the shaft 12 may be any type of light source, but may include a light emitting diode or an array of light emitting diodes. The light emitting diode or array of light emitting diodes may emit, e.g., white light. The relatively low power requirements for a light emitting diode, or for an array of light emitting diodes, as compared to the power requirements for the light source of a conventional endoscope system, enables the power source to be positioned at the distal end 12a of the shaft 12.

As mentioned above, the electric cable 20 in the shaft 12 may also include a data transfer cable 24. A distal end of the data transfer cable 24 is coupled to the image capture device 28 that is mounted on the distal end 12a of the shaft 12. A proximal end of the data transfer cable 24 is coupled to a video processing module 30 disposed within the control module 14. In this embodiment, the video processor 30 is configured to receive data signals from the image capture device 28 via the data transfer cable 24. Alternatively, the shaft 12 may not have a data transfer cable 24 but rather a wireless receiver and transmitter arrangement that enables the data to be transferred wirelessly.

According to one embodiment of the present invention, the shaft 12 may also include a working channel 16 that extends from the distal end 12a of the shaft 12 to the proximal end 12b of the shaft 12. At the distal end 12a of the shaft 12 is a working channel orifice 16a that leads into the working channel 16. The working channel 16 communicates with a working channel passage 16c disposed in the control module 14, so that the working channel 16 is accessible to a user via the working channel passage 16c in the control module 14. The working channel 16 may be configured to permit the passage of small endoscopic tools or the like, such as a cutting blade, thereby enabling a user to manipulate tissue positioned adjacent to the distal end 12a of the shaft 12 through the shaft 12 and without removing the distal end 12a of the shaft 12 from the patient's body.

According to one embodiment of the present invention, the shaft 12 also includes an irrigation/aspiration channel 32 that extends from the distal end 12a of the shaft 12 to the proximal end 12b of the shaft 12. At the distal end 12a of the shaft 12 is an irrigation/aspiration channel orifice 32a that leads into the irrigation/aspiration channel 32. The irrigation/aspiration channel 32 may be coupled to or in communication with an irrigation/aspiration system 19 disposed in the control module 14 and/or the power module 50 (described below in connection with FIG. 2). The irrigation/aspiration channel 32 is configured to convey fluid in a first direction through the irrigation/aspiration channel 32, e.g., towards the distal end 12a of the shaft 12, in order to irrigate a surgical site, and/or to convey fluid in the opposite direction through the irrigation/aspiration channel 32, e.g., away from the distal end 12a of the shaft 12, in order to aspirate a surgical site.

According to one embodiment of the present invention, the shaft 12 also defines at least one steering cable for steering at least a portion of the shaft 12. In one embodiment, the entire length of the shaft 12 is steerable, while according to other embodiments, only a portion of the shaft 12, such as a portion adjacent to the distal end 12a of the shaft 12, is steerable. In the example embodiment shown, the shaft 12 includes a first steering cable 34 and a second steering cable 36. The first steering cable 34 is configured to steer the shaft 12 in first and second directions that are 180 degrees apart relative to each other, e.g., north-south, while the second steering cable 36 is configured to steer the shaft 12 in third and fourth directions that are 180 degrees apart relative to each other and that are 90 degrees apart relative to the first and second directions, e.g., east-west. It should be understood that reference herein to north, south, east and west is made to a relative coordinate system. Advantageously, each of the first steering cable 34 and the second steering cable 36 extends from the distal end 12a of the shaft 12, or from a location near to the distal end 12a of the shaft 12, to the proximal end 12b of the shaft 12. It should be understood, however, that while a single steering cable is shown and described herein for steering the shaft 12 in each of the above-mentioned directions, other embodiments of the present invention may employ more than one steering cable for these purposes, as is described below. The steering cables may be arranged and configured as described, for example, in U.S. patent application Ser. No. 09/510,923, entitled "A Carriage Assembly for Controlling a Steering Wire Mechanism Within a Flexible Shaft," now issued as U.S. Pat. No 6,517,565, which is expressly incorporated herein in its entirety by reference thereto.

At the proximal end 12b of the shaft 12, the first steering cable 34 and the second steering cable 36 are coupled to drive elements of the control module 14 and/or the power module 50. One such arrangement, which is shown and described in FIG. 3 (discussed in greater detail below), provides that the first steering cable 34 and the second steering cable 36 are coupled to drive shafts 86, 92 of steering motors 84, 90.

Figure 6:
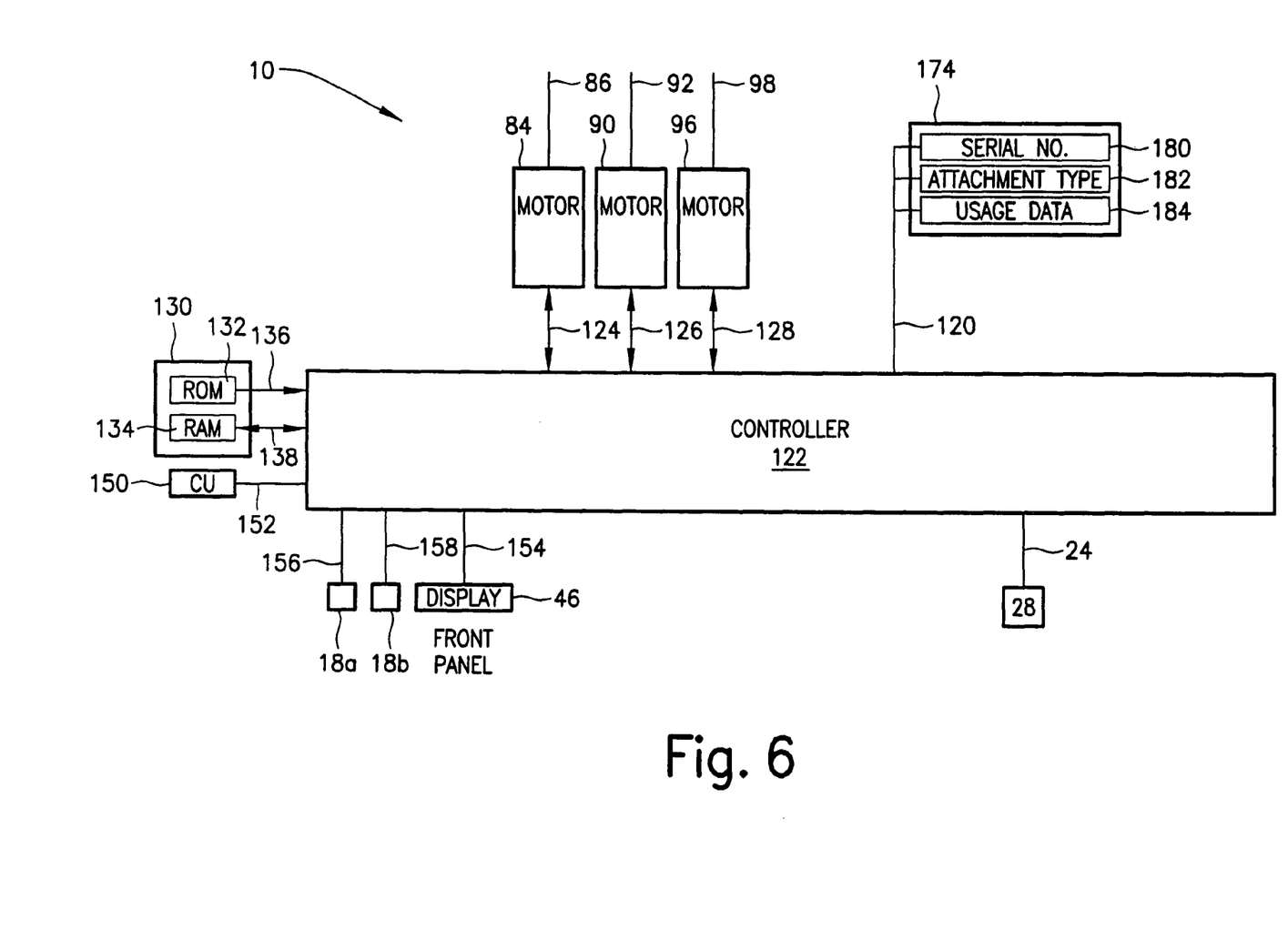
FIG. 6 is a schematic view of the endoscope system illustrated in FIGS. 1 and 2.

As mentioned above, FIG. 1 also illustrates a control module 14 for controlling the operation of the endoscope system 10. Advantageously, the control module 14 is a hand-held device that provides a control unit 150 having control mechanisms for a user to control certain functions of the endoscope system 10. Preferably, the control module 14, either separately or when connected to the shaft 12, is sterilizable, e.g., autoclavable. The control module 14 includes a controller 122 coupled to the various components of the shaft 12, the control module 14 and the power module 50. Advantageously, the controller 122 is configured to control additional functions of the endoscope system 10. FIG. 6, which is described in greater detail below, illustrates schematically one embodiment of the controller 122 connected to other components of the endoscope system 10.

According to the example embodiment of the present invention, the control module 14 includes a video processor 30 that receives data signals from the image capture device 28 via the data transfer cable 24 of the shaft 12 or via the wireless arrangement. The control module 14 may also include an integral display screen 46 that is coupled to the video processor 30. Upon receiving signals from the image capture device 28 via the data transfer cable 24, the video processor 30 is configured to process the signals and to display an image on the display screen 46 corresponding to the image received by the image capture device 28. According to one embodiment, the display screen 46 is moveable, e.g., rotatable, slidable, etc., relative to the control module 14. In this manner, the display screen 46 may be hidden from view when in the retracted position and may be viewable by a user when in an extended position. As previously mentioned, the control module 14 may be configured with appropriate materials and seals such that, when the display screen 46 in the retracted position, the control module 14 is sterilizable, e.g., autoclavable. Thus, the control module 14 including the display screen 46 may be protected from any environment which they may be employed in.

In addition to the video data received from the image capture device, the display screen 46 may display data corresponding to the operation of the endoscopic system 10. For instance, according to one embodiment, the display screen 46 provides an indication, via indicators such as indicators 18a and 18b (shown in FIG. 6 and described in greater detail below), corresponding to whether the system is turned on or off, or corresponding to the status of the steering cables, the irrigation/aspiration system 19, or any other aspect of the endoscopic system 10.

The control module 14 may also include an irrigation/aspiration system 19, such as a pump, that is configured to pump fluid in a first direction through the irrigation/aspiration channel 32 toward the distal end 12a of the shaft 12 in order to irrigate a surgical site. In addition, the control module 14 may include a second, or the same, pump (not shown) that is configured to pump fluid in the opposite direction through the irrigation/aspiration channel 32 away from the distal end 12a of the shaft 12 so as to aspirate the surgical site. The operation of the irrigation/aspiration system may be controlled by an irrigation/aspiration control switch 39 of a control unit 150 of the control module 14. The pump may be powered by the power source 44 in the control module 14, by the power source 62 in the power module 50, or by any other power source.

The control module 14 is coupled to one end 48a of a power transfer cable 48. The power transfer cable 48 may be fixedly or detachably coupled to the control module 14. Additional features of the power transfer cable 48 are described in connection with FIG. 2 below.

The control module 14 may also include, as part of the control unit 150, a steering controller 1300, a switch 312 and a two-way rocker 314. The steering controller 1300, the switch 312 and the two-way rocker 314 are described in more detail below in connection with FIG. 3.

Figure 2:
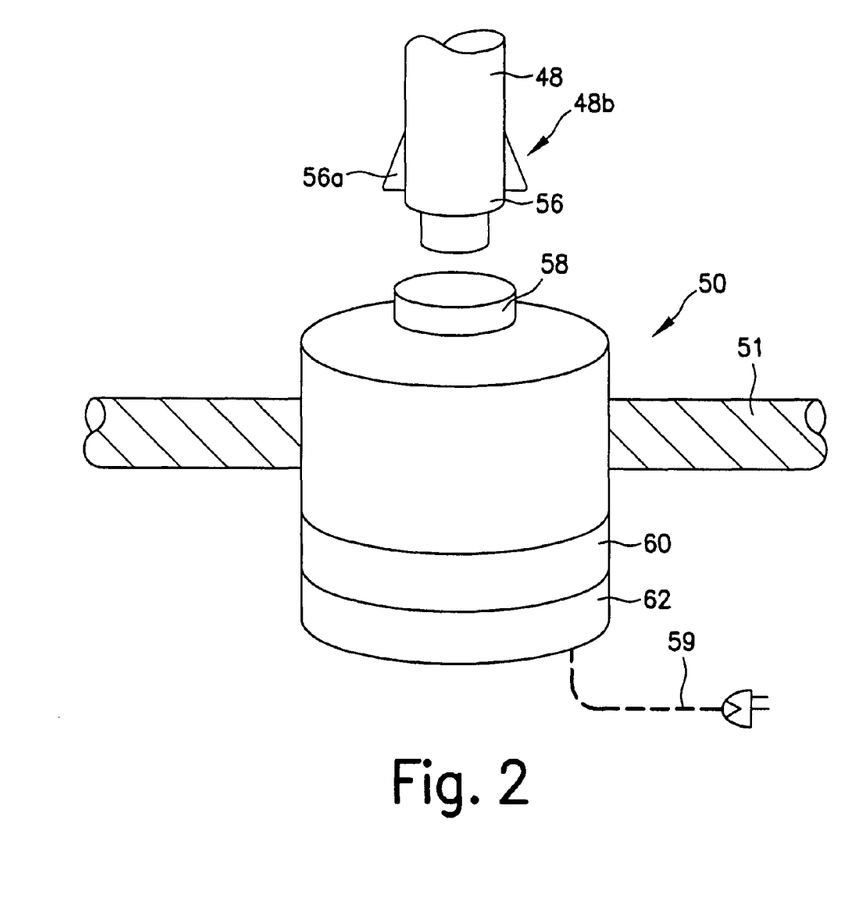
FIG. 2 is a perspective view of additional components of the endoscope system illustrated in FIG. 1.

FIG. 2 illustrates a power module 50 to which the control module 14 may be fixedly or detachably coupled. Although the example embodiment described herein includes the power module 50 being detachably coupled to the control module 14, it should be appreciated that, in alternative embodiments of the present invention, the power module 50 may be fixedly coupled to the control module 14. In this embodiment, the power module 50 may be worn by a user, such as by using belt 51.

The control module 14 is coupled to the power module 50 via a power transfer cable 48. As illustrated in FIG. 2, the power transfer cable 48 may be detachably coupled by a coupling 56 at an end 48b of the power transfer cable 48 to a corresponding coupling 58 of the power module 50. According to one embodiment, the coupling 56 may include a key structure 56a to properly orient the coupling 56 to the mating and complementary coupling 58 disposed on the power module 50. Such key structure 56a may be provided on either one, or both, of the coupling 56 and the mating and complementary coupling 58 disposed on the power module 50. For instance, the coupling 56 may include a quick-connect type connector, which may use, for example, a simple pushing motion to engage the coupling 56 of the power transfer cable 48 to the coupling 58 of the power module 50. Seals may be provided in order to provide a fluid-tight seal between the interior of the coupling 56 and the environment. In an alternative embodiment, the power transfer cable 48 is fixedly coupled both at its first end 48a to the control module 14 (see FIG. 1), and at its second end 48b to the power module 50.

Figure 5:
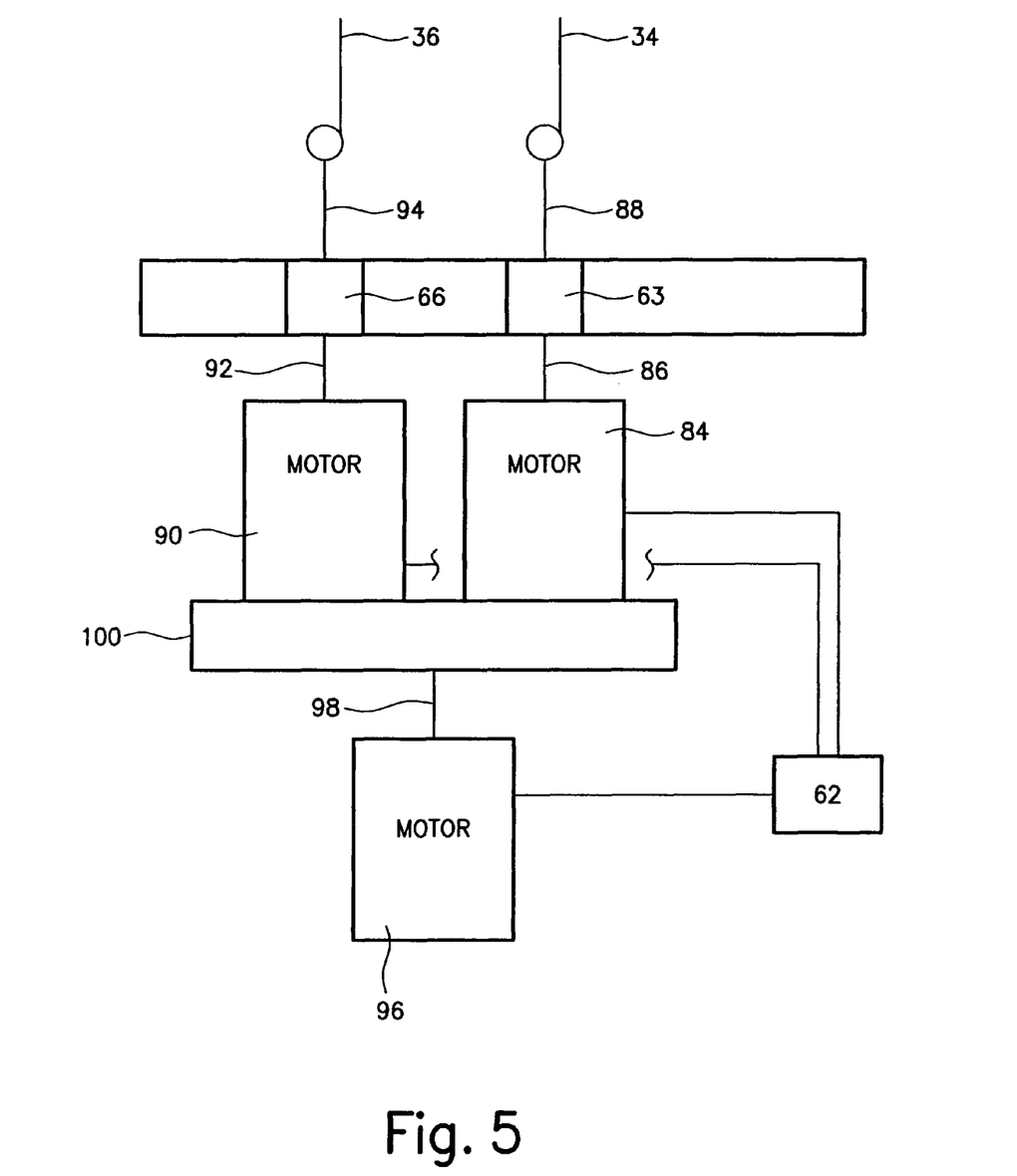
FIG. 5 is a schematic view illustrating a motor arrangement of the endoscope system illustrated in FIG. 2.

Advantageously, the power module 50 also houses steering and drive motors. For instance, according to one embodiment of the present invention, the power module 50 houses several steering motors for operating the steering cables 34, 36 of the shaft 12. One example embodiment of such an arrangement of steering motors is illustrated in FIG. 5, which is described in greater detail below. In addition, according to one embodiment of the present invention, the power module 50 houses a drive motor for operating the irrigation/aspiration system 19, etc.

In addition, the power module 50 may include a fluid reservoir 60 and a power source 62, such as a battery. According to one embodiment, the fluid reservoir 60 and the power source 62 are removable from the power module 50. In this manner, the fluid reservoir 60 may be refilled with fluid, e.g., water, as needed. According to one embodiment of the present invention, the fluid reservoir 60 may provide fluid to be pumped to a surgical site by an irrigation/aspiration system 19. Alternatively, the fluid reservoir 60 may store fluid removed from a surgical site by the irrigation/aspiration system 19. In this embodiment, the fluid reservoir 60 may be removed from the power module 50 in order to be emptied of its contents. In addition, the power source 62 may be removable from the power module 50 in order to be recharged as needed. As previously mentioned, the power source 62 may provide power, according to various embodiments of the present invention, to the light source 26 and the image capture device 28. In this embodiment, however, the power source 62 provides power to the controller 122 and/or the irrigation/aspiration system 19 and/or the steering and drive motors, etc. disposed in the control module 14 and the power module 50. According to still another embodiment, the power module 50 includes a power cord 59 that enables the power module 50 to be plugged into an electrical socket (not shown) or other conventional power source, thereby eliminating the need for the power source 62 or providing back-up power for the power source 62.

Referring now to FIG. 6, there is seen a schematic view of the endoscopic system 10. The controller 122 may be disposed in the control module 14, and is configured to control various functions and operations of the endoscopic system 10. A memory unit 130 is provided and may include memory devices, such as, a ROM component 132 and/or a RAM component 134 for storing programs or algorithms employed by the controller 122. ROM component 132 is in electrical and logical communication with controller 122 via line 136, and RAM component 134 is in electrical and logical communication with controller 122 via line 138. RAM component 134 may include any type of random-access memory, such as, for example, a magnetic memory device, an optical memory device, a magneto-optical memory device, an electronic memory device, etc. Similarly, ROM component 132 may include any type of read-only memory, such as, for example, a removable memory device, such as a PC-Card or PCMCIA-type device. It should be appreciated that ROM component 132 and RAM component 134 may be embodied as a single unit or may be separate units and that ROM component 132 and/or RAM component 134 may be provided in the form of a PC-Card or PCMCIA-type device.

Figure 3:
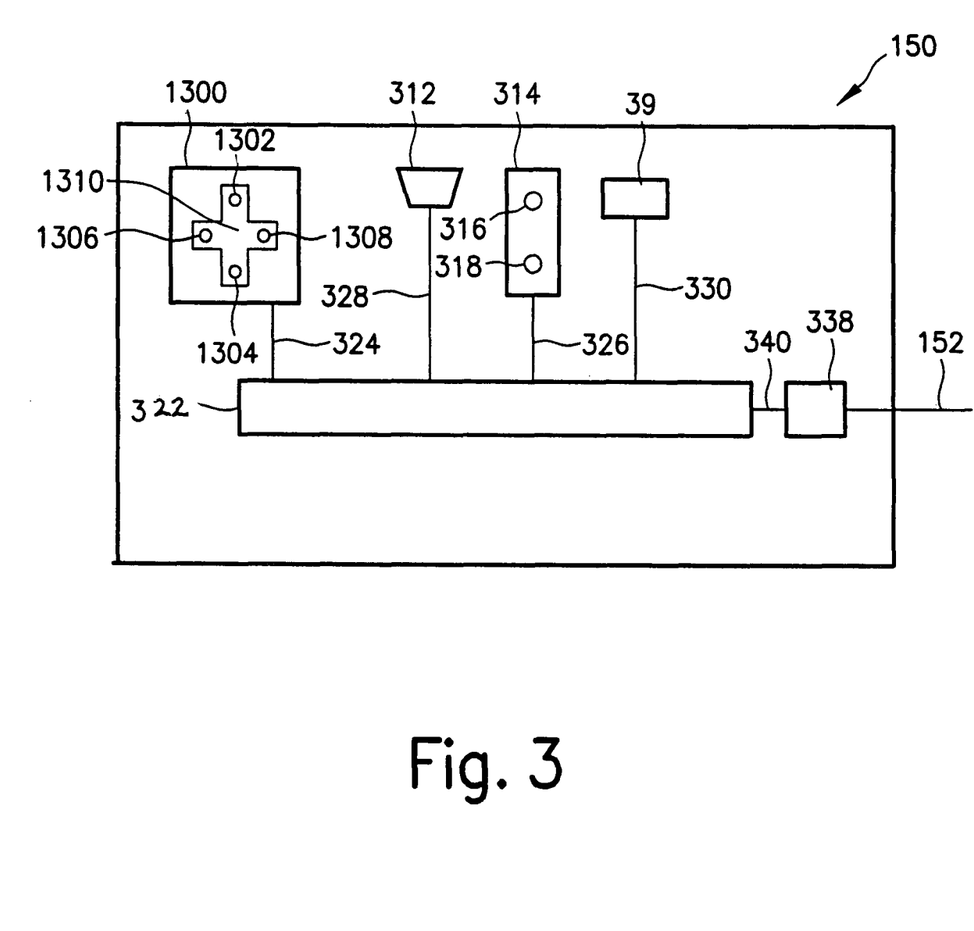
FIG. 3 is a schematic view of a control unit of the endoscope system illustrated in FIG. 1.
Figure 7:
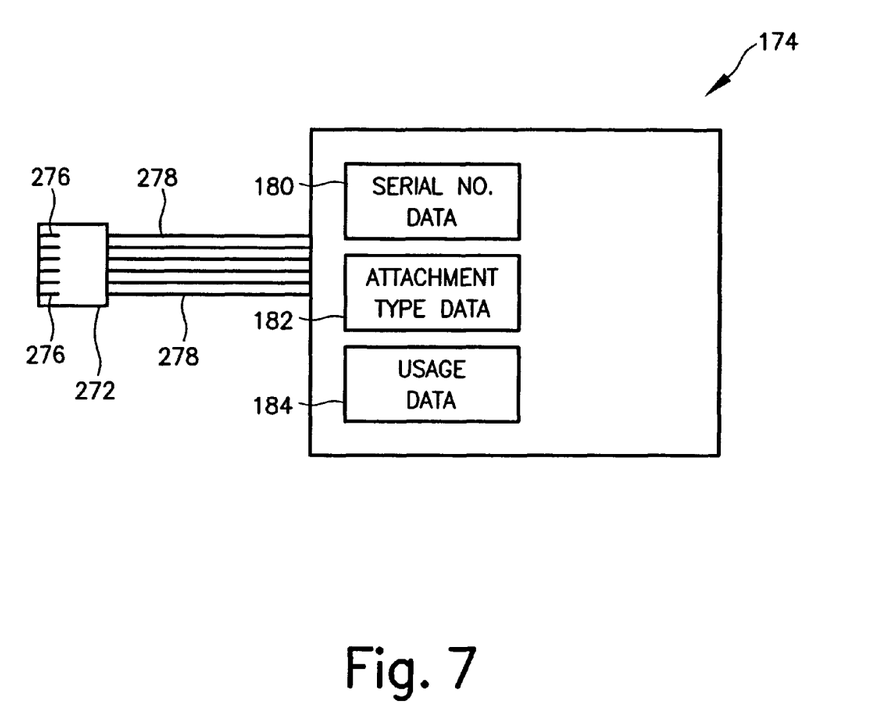
FIG. 7 is a schematic view of a memory device of the endoscope system illustrated in FIG. 1.

The controller 122 is further connected to the display screen 46 via line 154 and to the indicators 18a, 18b via respective lines 156, 158. Lines 124, 126, 128 electrically and logically connect controller 122 to motors 84, 90, 96, respectively, the function of which is described in greater detail below. A control unit 150, which may include the control features of the control module 14 such as a steering controller 1300, the irrigation/aspiration system switch 39, etc. is electrically and logically connected to controller 122 via line 152. Additional features of the control unit 150 are illustrated in FIG. 3, which is described in greater detail below. In addition, the controller 122 may be electrically and logically connected by data transfer cable 24 to the image capture device 28. Furthermore, the controller 122 may be electrically and logically connected by line 120 to one or more memory units 174, an example of which is illustrated in FIG. 7 and described in greater detail below.

As described above, the power module 50 includes motors configured to drive the steering cables 34, 36. FIG. 5 illustrates schematically one possible arrangement of motors within the power module 50. In the example embodiment illustrated schematically in FIG. 5, three electric motors 84, 90, 96, each operating via a power source such as power source 62, are disposed in the power module 50. It should be appreciated, however, that any appropriate number of motors may be provided for this purpose, and the motors may operate via battery power, line current, a DC power supply, an electronically controlled DC power supply, AC power, etc. It should also be appreciated that the steering motors 84, 90 may be connected to a DC power supply, which is in turn connected to line current and which supplies the operating current to the motors.

According to one embodiment of the present invention, at the proximal end 12b of the shaft 12, the first steering cable 34 and the second steering cable 36 are coupled to drive elements (not shown) of the control module 14 that in turn are coupled to drive shafts 86, 92 of steering motors 84, 90, located in the power module 50. It should be appreciated that, according to various other embodiments of the present invention, drive shafts 86, 92 and steering motors 84, 90 may instead be located in the control module 14.

Referring to FIG. 5, an output shaft 86 of a motor 84 engages a connector 63 of the coupling 56 of the power transfer cable 48 when the coupling 56 is engaged with the power module 50 to thereby drive the first steering cable 34. It should be understood that, while only a single steering cable 34 is shown and described for steering the shaft 12 in the north-south direction, the present invention may employ, in accordance with an alternative embodiment of the invention, a pair of steering cables via a pulley arrangement for this purpose. In addition, an output shaft 92 of a motor 90 engages the connector 66 of the coupling 56 when the coupling 56 is engaged with the power module 50 to thereby drive the second steering cable 36. Again, it should be understood that, while only a single steering cable 36 is shown and described for steering the shaft 12 in the east-west direction, the present invention may employ, in accordance with an alternative embodiment of the invention, a pair of steering cables via a pulley arrangement for this purpose. The motors 84, 90 may be secured on a carriage 100, which is selectively movable via an output shaft 98 of a motor 96 between a first position and a second position to selectively engage and disengage the motors 84, 90 to thereby permit the shaft 12 to become taut and steerable or limp as necessary. It should be appreciated that other mechanical, electrical or electromechanical mechanisms may be used to selectively engage and disengage the steering mechanism. The motors may be arranged and configured as described, for example, in U.S. patent application Ser. No. 09/510,923, entitled "A Carriage Assembly for Controlling a Steering Wire Mechanism Within a Flexible Shaft," now issued as U.S. Pat. No. 6,517,565, which is expressly incorporated herein in its entirety by reference thereto.

Figure 4:
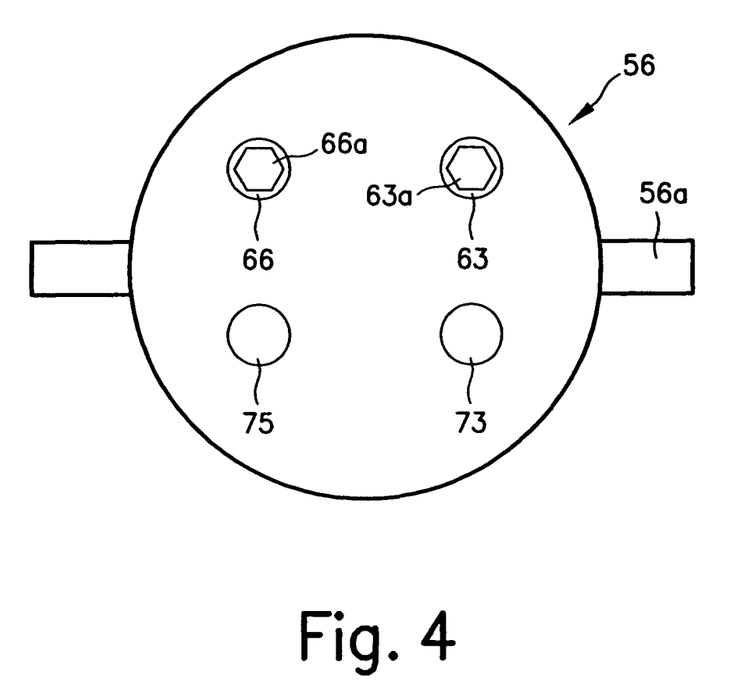
FIG. 4 is a front end view of a coupling of a power transfer cable illustrated in FIG. 2.

Referring now to FIG. 4, there is illustrated a front end view of the coupling 56 of the power transfer cable 48. The coupling 56 includes a first connector 63 and a second connector 66, each rotatably secured to the coupling 56. Each of the connectors 63, 66 includes a respective recess 63a, 66a. Each of the recesses 63a, 66a may be hexagonally shaped. It should be appreciated, however, that the recesses 63a, 66a may have any shape and configuration to non-rotatably couple and rigidly attach the connectors 63, 66 to respective drive shafts 86, 92 of the motor arrangement contained within the power module 50, as more fully described below. It should be appreciated that complementary projections may be provided on respective drive shafts 86, 92 of the motor arrangement to thereby drive the steering cables 34, 36 of the shaft 12 as described below. It should also be appreciated that the recesses may be provided on the drive shafts 86, 92 and complementary projections may be provided on the connectors 63, 66. Any other coupling arrangement configured to non-rotatably and releasably couple the connectors 63, 66 and the drive shafts 86, 92 of the motor arrangement may be provided. According to one embodiment, the connectors 63, 66 engage with the above-described elements so as to apply tensile forces on the steering cables 34, 36 to thereby steer the distal end 12a of the shaft 12. FIG. 4 also illustrates a fluid connector 73. The fluid connector 73 provides a connection from the fluid reservoir 60 in the power module 50 to the irrigation/aspiration system 19 in the control module 14. In addition, FIG. 4 illustrates a power connector 75. In the above-described embodiments wherein the power source 62 provides power to components of the shaft 12 and the control module 14, the power connection 75 provides a connection from the power source 62 to these components.

Referring now to FIG. 3, there is seen a schematic view of the control unit 150 of the control module 14. In accordance with one embodiment of the present invention, the control unit 150 includes a steering controller 1300, having a plurality of switches 1302, 1304, 1306, 1308 arranged under a four-way rocker 1310. The operation of the switches 1302, 1304, via the rocker 1310, controls the operation of the first steering cable 34 via the steering motor 84. Similarly, the operation of the switches 1306, 1308, via the rocker 1310, controls the operation of the second steering cable 36 via the steering motor 90. It should be appreciated that the rocker 1310 and the switches 1302, 1304, 1306, 1308 are arranged so that the operation of the switches 1302, 1304 steers the shaft 12 in the north-south direction and that the operation of the switches 1306, 1308 steers the shaft 12 in the east-west direction. Again, reference herein to north, south, east and west is made to a relative coordinate system. Alternatively, a digital joystick, analog joystick, etc. may be provided in place of the rocker 1310 and the switches 1302, 1304, 1306, 1308. Potentiometers or any other type of actuator may also be used in place of the switches 1302, 1304, 1306, 1308.

Furthermore, the control unit 150 may include a switch 312, which further controls certain functions of the endoscope system 10 in accordance with an operating program or algorithm employed by the controller 122. For instance, the operation of switch 312 may control the operation of the motor 96 to selectively engage and disengage the steering mechanism, or may control the activation of the light source 26 or the image capture device 28. The control unit 150 may also be provided with a switch 39, the operation of which may further control other functions of the endoscope system 10 in accordance with the operating program or algorithm employed by the controller 122. For example, operation of the switch 39 may control the activation of the irrigation/aspiration system 19. The control unit 150 may also include a two-way rocker 314 having first and second switches 316, 318 operable thereby. The operation of these switches 316, 318 may control still other functions of the endoscope system 10 in accordance with the operating program or algorithm employed by the controller 122. For example, operation of the two-way rocker 314 may control a zoom or magnification function of the image capture device 28.

The control unit 150 may include a separate controller 322, which is electrically and logically connected with the switches 302, 304, 306, 308 via line 324, with the switches 316, 318 via line 326, with switch 312 via line 328 and with switch 39 via line 330. The indicators 18a, 18b and the display device 46 may be electrically and logically connected to the controller 322 rather than controller 122.

According to one embodiment of the present invention, one or more of the shaft 12, the control module 14 and the power module 50 may include a memory unit, such as memory unit 174 illustrated schematically in FIG. 7. The memory unit 174 may store information as described, for example, in U.S. patent application Ser. No. 09/723,715, filed on Nov. 28, 2000, now issued as U.S. Pat. No. 6,793,652,U.S. patent application Ser. No. 09/836,781, filed on Apr. 17, 2001, U.S. patent application Ser. No. 09/887,789, filed on Jun. 22, 2001, and U.S. patent application Ser. No. 10/099,634, filed on Mar. 15, 2002 each of which is expressly incorporated herein by reference in its entirety. For instance, as illustrated in FIG. 7, the memory unit 174 may include a data connector 272 that includes contacts 276, each electrically and logically connected to memory unit 174 via a respective line 278. Memory unit 174 is configured to store, for example, a serial number data 180, an attachment type identifier (ID) data 182 and a usage data 184. Memory unit 174 may additionally store other data. Both the serial number data 180 and the ID data 182 may be configured as read-only data. In the example embodiment, serial number data 180 is data uniquely identifying the particular component, whereas the ID data 182 is data identifying the type of the component, such as, for example, a shaft. The usage data 184 represents usage of the particular component, such as, for example, the number of times the shaft 12 has been employed or the number of times that the light source 26 has been activated. It should be appreciated that the shaft 12 may be designed and configured to be used a single time or, in such embodiments wherein the shaft 12 is sterilizable or autoclavable, multiple times. The control module 14 and/or the power module 50 may also be designed and configured to be used a predetermined number of times. Accordingly, the usage data 184 may be used to determine whether the shaft 12 has been used and/or whether the number of uses has exceeded the maximum number of permitted uses. According to one embodiment, an attempt to use the shaft 12 (or the control module 14 and the power module 50) after the maximum number of permitted uses has been reached may generate an ERROR condition.

Figure 10:
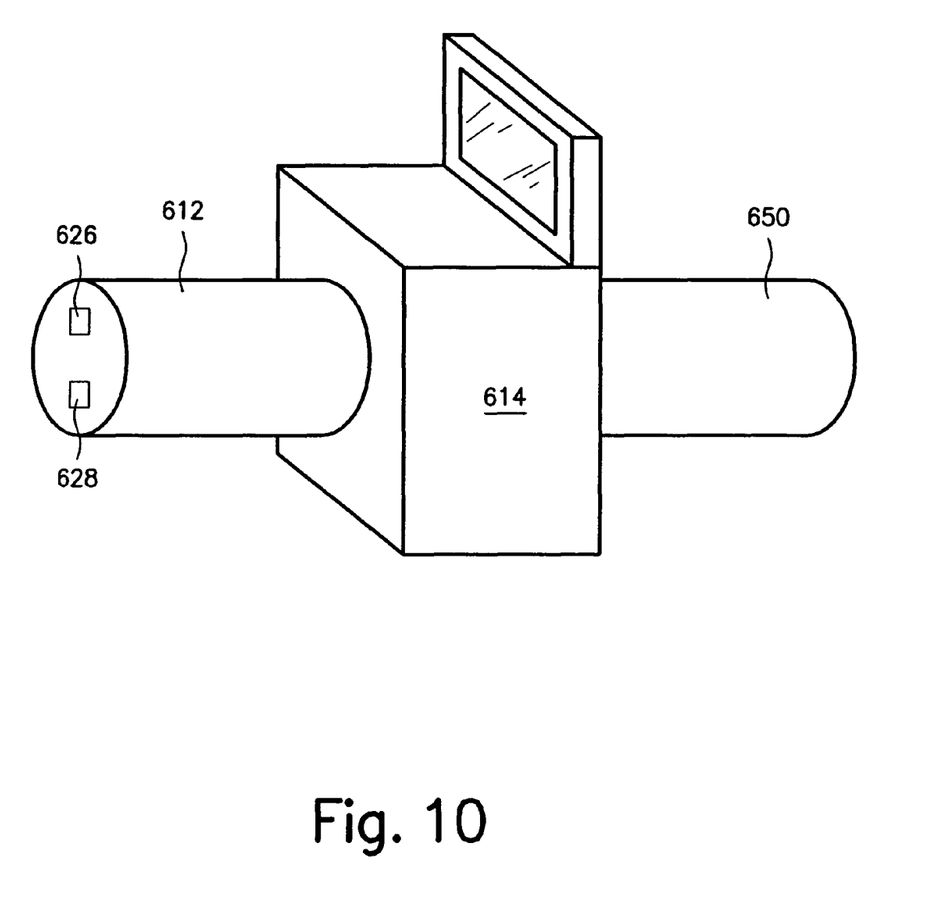
FIG. 10 is a perspective view that illustrates several components of a hand-held surgical system, according to still another example embodiment of the present invention.

While the present invention has been described hereinabove in connection with endoscope systems, it should be recognized that other types of surgical systems may be employed for various different types of surgical procedures, e.g., proctoscopy, anoscopy, etc. For instance, FIG. 10 is a diagram that illustrates various components of a surgical system 600. The surgical system 600 may be configured as a hand-held device and may be employed in a manner that is different from an endoscope system. The surgical system 600 may include a shaft 612 that is connected to a control module 614, which in turn is connected to a handle 650. For the purposes of clarity, other features of the surgical systems that are illustrated in FIGS. 1 to 9, e.g., the control module, display screen, power sources, etc., are not illustrated in FIG. 10. However, it should be recognized that, in accordance with various embodiments of the present invention, any or all of these features may be employed in the surgical system 600.

The present invention, in accordance with various embodiments thereof, provides advantages over conventional surgical, e.g., endoscope, systems. For instance, a conventional endoscope is typically cleaned or disinfected prior to use within a patient in conformance with a standard referred to as high-level disinfectance, rather than sterilization. Sterilization provides a greater degree of cleanliness, and thus a high standard of patient safety, than high-level disinfectance. Conventional endoscopes typically can not be sterilized prior to use within a patient because the materials employed in the manufacture of conventional endoscopes are not sterilizable, and because conventional endoscope are typically not adequately sealed to withstand a sterilization process. Unlike conventional endoscope systems, various components of the endoscope system 10 of the present invention, most particularly the shaft 12, the light source 26, the image capture device 28, the control module 14 and in some instances the power module 50, may be sterilizable or autoclavable, thereby providing a higher level of safety to a patient. Furthermore, because various components of the endoscope system 10 of the present invention, e.g., the shaft 12, the light source 26, the image capture device 28, the control module 14 and the power module 50, may be sterilizable or autoclavable, these components can be used more than once and on more than one patient, providing significant cost savings as compared to conventional endoscope systems that must be discarded after one use.

In addition, according to some embodiments, the surgical systems of the present invention employ a light emitting diode or an array of light emitting diodes as the light source 26 at the distal end 12a of the shaft 12. Thus, the surgical systems of the present invention may provide for a more efficient use of the light as compared to conventional surgical, e.g., endoscope, systems employing a light source outside of the patient's body and a fiber-optic bundle to transport the light through the shaft, since these conventional surgical, e.g., endoscope, systems lose a large portion of the light before the light reaches the surgical site. In addition, the use by the present invention of a light emitting diode or an array of light emitting diodes provides satisfactory illumination of a surgical site while requiring very little power. Thus, according to one embodiment, a power source may be provided at the distal end 12a of the shaft 12, or at any other location along the shaft 12, in the control module 14 or in the power module 50.

In addition, according to some embodiments, the surgical system of the present invention employs a display screen 46 that is integral with the hand-held control module 14, thereby replacing the bulkiness and complexity of a separate television monitor for this purpose. Furthermore, according to some embodiments, the surgical system of the present invention employs power sources, motors, etc. that are integral with either the shaft 12, the control module 14 or the power module 50, enabling the surgical system to be self-contained, e.g., requiring no additional external power supplies, drive mechanisms, etc.

Thus, the several aforementioned objects and advantages of the present invention are most effectively attained. Those skilled in the art will appreciate that numerous modifications of the exemplary embodiment described hereinabove may be made without departing from the spirit and scope of the invention. Although a single exemplary embodiment of the present invention has been described and disclosed in detail herein, it should be understood that this invention is in no sense limited thereby.

What is claimed is:

1. A surgical system, comprising:
a shaft having a distal end and a proximal end, an interior of the shaft having a fluid-tight seal from the environment at each of the distal end and the proximal end so as to be sterilizable for re-use, the shaft including first and second steering cables;
a power module including a coupling having first and second connectors, the first and second connectors rotatable in relation to the coupling and connected to the first and second steering cables of the shaft, the power module including selectively engageable first and second steering motors operably coupled to the first and second connectors, respectively, the first and second steering motors secured to a movable carriage that is movable from a first position to a second position for selectively engaging the first and second motors to selectively rotate at least one of the first and second connectors for steering at least a portion of the shaft;
an image capture device configured to receive image data from the distal end of the shaft; and
a light-emitting diode configured to provide light at the distal end of the shaft,
wherein the image capture device and the light-emitting diode are mounted to the distal end of the shaft and fluid-tightly sealed from the environment by the shaft so as to be sterilizable for re-use.

2. The surgical system of claim 1, wherein the shaft is sized and configured for endoscopic insertion into a patient's body.

3. The surgical system of claim 1, wherein the shaft is flexible.

4. The surgical system of claim 1, wherein the light emitting diode is part of an array of light-emitting diodes.

5. The surgical system of claim 1, wherein the light emitting diode, the image capture device and the shaft are, as a unit, at least one of sterilizable and autoclavable.

6. The surgical system of claim 1, wherein the image capture device is one of a camera and a CCD.

7. The surgical system of claim 1, further comprising a power source for providing power to the light-emitting diode, the power source located at the distal end of the shaft.

8. The surgical system of claim 1, wherein the shaft is autoclavable.

9. The surgical system of claim 1, further comprising a control module coupled to a proximal end of the shaft.

10. The surgical system of claim 9, wherein the control module is detachably coupled to the proximal end of the shaft.

11. The surgical system of claim 9, wherein the control module is one of sterilizable and autoclavable.

12. The surgical system of claim 9, wherein the control module includes a video processor.

13. The surgical system of claim 12, wherein the shaft includes a data transfer cable, and wherein the image data received by the image capture device is transmitted via the data transfer cable to the video processor.

14. The surgical system of claim 12, further comprising a wireless arrangement configured to transfer image data received by the image capture device to the video processor.

15. The surgical system of claim 9, further comprising a display screen integrally mounted to the control module.

16. The surgical system of claim 9, wherein the shaft includes an irrigation/aspiration channel, and wherein the control module includes an irrigation/aspiration system for conveying fluid through the irrigation/aspiration channel of the shaft.

17. The surgical system of claim 9, wherein the control module includes a control unit for enabling a user to control the surgical system.

18. The surgical system of claim 9, wherein the control module includes a controller for automatically controlling the surgical system.

19. The surgical system of claim 9, wherein the power module is configured to provide power to components housed in at least one of the control module and the shaft.

20. The surgical system of claim 19, wherein, when the power module is configured to provide power to components housed in the shaft, the shaft includes a power transfer cable.

21. The surgical system of claim 20, wherein the power module includes at least one of drive motors for driving the steering motors and a power source.

22. The surgical system of claim 1, wherein the power module includes a third motor including an output shaft coupled to the carriage for selectively moving the carriage between the first and second positions.

23. The surgical system of claim 1, wherein the shaft includes a working channel for permitting the passage of tools through the shaft.

* * * * *